United States Patent [19]

Schiff et al.

[11] Patent Number: 4,569,332
[45] Date of Patent: Feb. 11, 1986

[54] METHOD AND APPARATUS FOR TREATING A HEART PATIENT THROUGH THE COORDINATING EFFORTS OF BALLOON PUMPING AND DISPENSING CATHETERS

[75] Inventors: Peter Schiff, Rte. 7, Cookeville, Tenn. 38501; Cary L. Lambert, Dallas, Tex.

[73] Assignee: Peter Schiff, Cookeville, Tenn.

[21] Appl. No.: 484,432

[22] Filed: Apr. 13, 1983

[51] Int. Cl.⁴ .................... A61B 19/00; A61M 25/00
[52] U.S. Cl. .................................................. 128/1 D
[58] Field of Search ............................ 128/1 D, 4–6, 128/344; 604/95–103, 164, 280

[56] References Cited

U.S. PATENT DOCUMENTS

| | | | |
|---|---|---|---|
| 4,024,873 | 5/1977 | Antoshkiw et al. | 604/96 |
| 4,149,535 | 4/1979 | Volder | 604/164 X |
| 4,154,227 | 5/1979 | Krause et al. | 128/1 D |
| 4,271,839 | 6/1981 | Fogarty et al. | 128/344 |
| 4,299,226 | 11/1981 | Banka | 128/344 |
| 4,445,892 | 5/1984 | Hussein et al. | 604/101 |
| 4,456,000 | 6/1984 | Schjeldahl et al. | 128/1 D |

Primary Examiner—Dalton L. Truluck
Attorney, Agent, or Firm—Louis Weinstein

[57] ABSTRACT

Method and apparatus for treating heart patients employing the coordinated efforts of dispensing and balloon pumping catheters. A balloon pumping catheter is inserted and properly positioned within the aortic arch. The balloon catheter has a lumen through which a dispensing catheter extends. The distal end of the dispensing catheter is guided to the operative position, preferably by means of a guide wire extending through the dispensing catheter. The guide wire is removed prior to a dispensing operation. Measured doses of a medicinal solution, such as, for example, a blood thinner, are periodically dispensed through the dispensing catheter and in coordination with the pumping operation. A single pumping source may be utilized for powering the balloon pumping and dispensing operations. An adjustable delay provided between the source and one of the catheter assemblies provides the proper coordination between the balloon pumping and dispensing operations. The dispensing catheter may include a small dilatation balloon having a first lumen for dispensing a medicinal solution and a second lumen for inflating the dilatation balloon.

18 Claims, 9 Drawing Figures

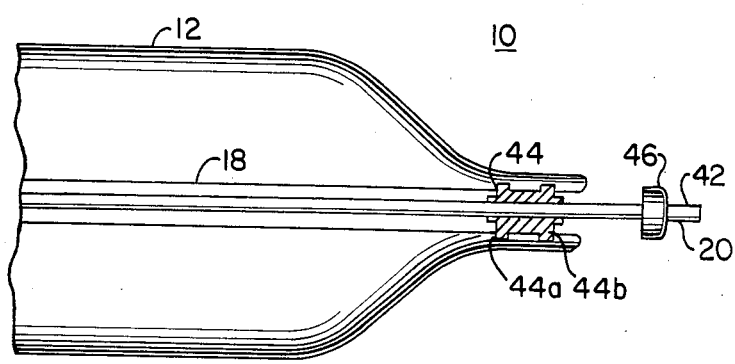
FIG. 3
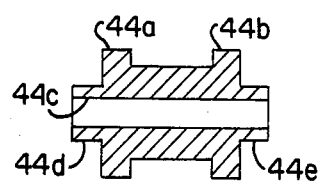
FIG. 3b
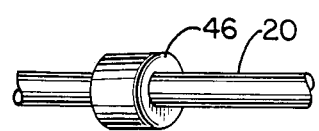
FIG. 3a
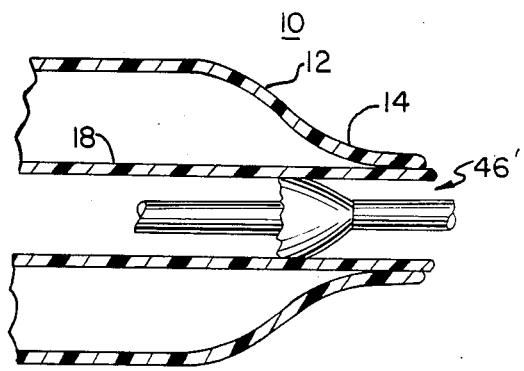
FIG. 4a
FIG. 4b
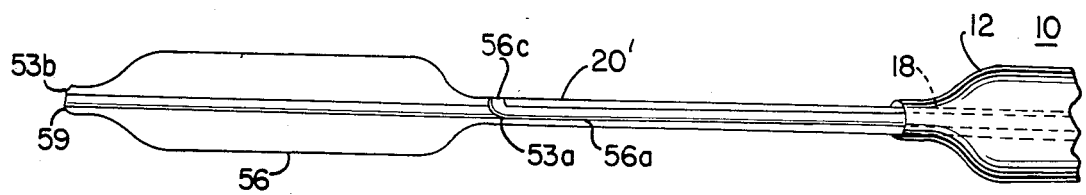
FIG. 5

METHOD AND APPARATUS FOR TREATING A HEART PATIENT THROUGH THE COORDINATING EFFORTS OF BALLOON PUMPING AND DISPENSING CATHETERS

FIELD OF THE INVENTION

The present invention relates to medical treatment for heart patients and, more particularly, to method and apparatus for treating heart patients through the coordinated efforts of a balloon pumping catheter and a dispensing catheter.

BACKGROUND OF THE INVENTION

Intra-aortic balloon pumping devices are well-known to the medical profession and are widely used for purposes of aiding a weakened heart in the blood pumping function. It is also conventional to use dispensing catheters for localized treatment of internal regions of the body and such dispensing catheters have been employed for purposes of dispensing medicinal solutions such as, for example, blood thinners, into the coronary arteries. However, these devices have never been used together in a coordinated effort to treat a heart patient.

BRIEF DESCRIPTION OF THE INVENTION

The present invention is characterized by comprising method and apparatus for treating a heart patient through the coordinated efforts of intra-aortic balloon pumping catheter and dispensing catheter assemblies.

The balloon pumping catheter, in the preferred embodiment, is provided with a central lumen having an inner diameter which is greater than the outer diameter of a dispensing catheter. The intra-aortic balloon is inserted into the body over a guide wire and, after being properly positioned, typically near the region of the aortic arch, the dispensing catheter is inserted into the intra-aortic balloon and is guided by the guide wire. The dispensing catheter is advanced along the lumen and through the intra-aortic balloon and is guided by the guide wire, which extends beyond the distal end of the dispensing and balloon catheters. The dispensing catheter is guided along the guide wire and outwardly and beyond the open distal end of the intra-aortic balloon. The distal end of the guide wire is moved to the position where it is desired to place the distal end of the dispensing catheter and the dispensing catheter is guided along said guide wire until its distal end is moved to the desired position, whereupon the guide wire is removed.

A pump, arranged between the dispensing catheter and a source of medicinal solution, pumps measured doses of the solution through the dispensing catheter and to the desired location within the body. At the same time, the pumping means operates the balloon pump in synchronism with the pumping of the patient's weakened heart. A single pump means may be utilized to accomplish both functions. Delay means, preferably made adjustable, is provided between the balloon pumping mechanism and the dispenser pumping mechanism to provide proper timing therebetween.

The purpose of such coordinated means of dispensing solutions and pumping a balloon in synchronism is that the technique intentionally directs flow to the coronaries, which are primarily perfused during diastole, when the heart muscle relaxes. As the intra-aortic balloon inflates during diastole, it pushes oxygenated blood by retrograde flow into the coronaries. The dispensed solutions infused thereby are uniquely localized into the coronaries, instead of creating an undesired generalized effect on the patient.

A liquid-tight sliding seal is provided between the IAB lumen and the dispensing catheter to prevent the egress of body fluids through the IAB lumen.

The pumping mechanism may be arranged to continuously pump a first liquid such as a saline solution, and to periodically introduce the medicinal solution, such as a blood thinner together with the first-mentioned solution, if desired.

The dispensing catheter may be provided with blocking projections to prevent accidental reinsertion of the distal end of the dispensing catheter back into the IAB lumen.

The novel method and apparatus of the present invention may also utilize conventional IAB and dispensing catheter assemblies which are operated in the aforementioned coordinated fashion.

OBJECTS OF THE INVENTION AND BRIEF DESCRIPTION OF THE FIGURES

It is, therefore, one object of the present invention to provide novel method and apparatus for medical treatment of a heart patient employing the coordinated efforts of catheter dispensing means and balloon catheter pumping means.

Still another object of the present invention is to provide novel apparatus for treatment of a heart condition, comprising an intra-aortic balloon assembly having a lumen for slidably receiving a dispensing catheter movably positionable within the body of the patient for dispensing a medicinal liquid in coordination with balloon pumping.

The above, as well as other objects of the present invention, become apparent when reading the accompanying description and drawing in which:

FIG. 3 shows an enlarged sectional view showing a liquid-tight sliding seal and a locking member employed for preventing the telescoping of the dispensing catheter into the IAB lumen, which structures may be embodied in the system of FIG. 2.

FIG. 3a shows an enlarged perspective view of the blocking member of FIG. 3.

FIG. 3b shows an enlarged sectional view of the sliding seal and locking member of FIG. 3.

FIGS. 4a and 4b show two operating positions of another alternative embodiment for a blocking member and which is useful in understanding the manner in which the blocking member functions.

FIG. 5 is a plan view showing another embodiment of the present invention.

DETAILED DESCRIPTION OF THE INVENTION

Figure 1:
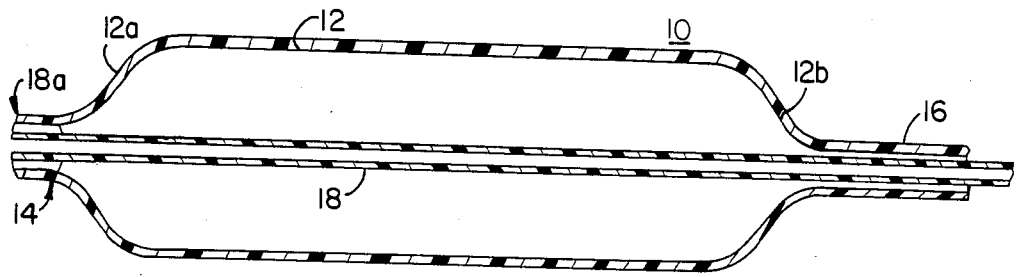
FIG. 1 shows a simplified diagram of an IAB incorporating the principles of the present invention and which is especially adapted for practicing the method of the present invention.

FIG. 1 shows an IAB 10 comprised of a balloon 12 formed of a flexible, substantially elastic material capable of being inflated without experiencing expansion when inflated under normal operating pressure.

The distal end 12a of balloon 12 tapers as shown and terminates in a tip 14. The proximal end 12b tapers as is shown and is joined to, and communicates with, the hollow interior of catheter tube 16 which is of a length sufficient to properly position balloon 12 within the body and yet have its proximal end (not shown) accessible at a location exterior to the body, for coupling with pumping means (not shown for purposes of simplicity) which provides positive and negative pressure pulses for respectively inflating and deflating balloon 12.

IAB 10 further incorporates a lumen 18 in the form of a hollow, elongated tube of relatively small diameter. The distal end 18a is secured at tip 14 and the lumen extends rearwardly through balloon 12 and catheter tube 16 and has its proximal end (not shown) accessible at a location external to the body. The isolation (i.e. gas-tight seal) between the interior of balloon 12 and catheter 16 and the interior of lumen 18 is maintained throughout the entire length of IAB 10.

Figure 1A:
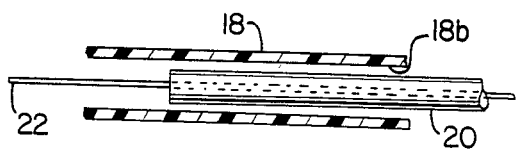
FIG. 1a shows an enlarged sectional view showing the manner in which the balloon lumen receives the dispensing catheter and guide wire.

The inner diameter of lumen 18, as shown best in FIG. 1a, is greater than the outer diameter of a dispensing catheter 20, this size difference being sufficient to allow the dispensing catheter 20 to be slidably inserted through and advanced along lumen 18. The distal end 18a of lumen 18 is open to permit dispensing catheter 20 (and guide wire 22) to be pushed through and beyond open end 18a.

The guide wire 22 is preferably utilized for properly positioning IAB 10 and dispensing catheter 20 in a manner to be more fully described.

Figure 2:
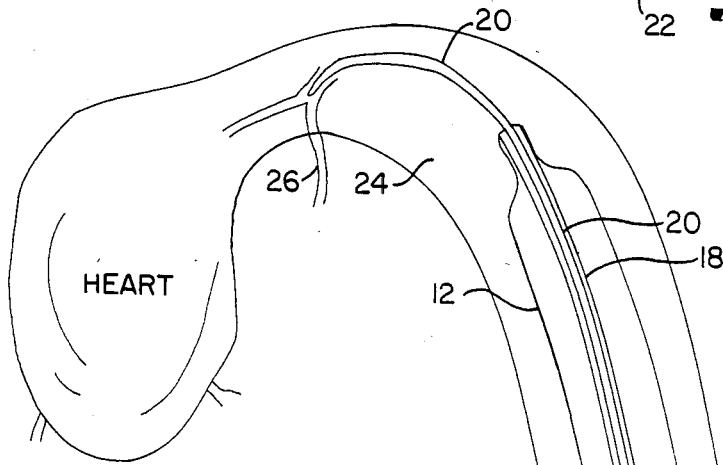
FIG. 2 shows the manner in which the IAB and dispensing catheter are employed in a coordinated manner for medical treatment of a patient.

FIG. 2 shows the manner in which the IAB 10 and dispensing catheter 20 are used in a coordinated fashion for treatment of a patient.

The manner of insertion and use of the assembly of FIG. 2 is as follows:

A small puncture is made in the femoral artery through the use of a hypodermic-type needle having a hollow center. The guide wire 22 is inserted through the hollow center of the needle and along the femoral artery until its distal end is located at the desired position. The hypodermic-type needle is removed and one or more dilator members are advanced over the guide wire and through the site of the puncture in order to enlarge the original puncture to a size sufficient to accommodate the IAB 10. The IAB is then inserted into the femoral artery over guide wire 22 until it is properly positioned within the aortic arch as shown as 24 in FIG. 2.

Thereafter, dispensing catheter 20 is inserted through the hollow lumen 18 until its distal end 20a extends through the open end 18a of lumen 18. The dispensing catheter 20 is thereafter guided still further beyond balloon tip 14 and into or at the mouth of a coronary artery 26. The guide wire 22 is then withdrawn and the balloon pumping and dispensing operations are initiated.

In one preferred embodiment, to obtain clot dissolution, a blood thinner such as Streptokinase is administered. Using the technique of the present invention, it is possible to support a patient having an established or an evolving infarction with IAB 10 and also to administer the blood thinner. This is accomplished by dispensing the blood thinner through the dispensing catheter 20 which has an outer diameter small enough to permit its adjustment and proper placement in the body, preferably through the IAB lumen 18 and with the aid of guide wire 22. The dispensing catheter 20 has sufficient rigidity so as not to be displaced from the root of the aorta. The dispensing operation is phased in such a manner as to instill a measured dosage during each diastolic inflationary phase. This is accomplished through the apparatus employed in FIG. 2 in which pulsatile pressure from the pressure source is delivered through input conduit 28 to the proximal end of catheter 16 and to a conduit 30 containing an adjustable pressure delay device 32 for coupling pressure pulses after a predetermined delay to a pressure amplifying apparatus 34, coupled with pump 36. A source of blood thinner is coupled through conduit 38 to input 36a of pump 36. A source of saline solution is coupled through conduit 40 through input 36b of pump 36. Shut-off valves 39 and 41 are provided in conduits 38 and 40 for selectively coupling the sources of solution to pump 36. One-way valves 43, 45 and 47 in conduits 38, 40 and 20 prevent reverse flow of solution in these conduits. To assure proper operation, the containers containing the saline solution and blood thinner solution are positioned above pump 36 to facilitate the flow of these solutions to pump 36 by gravity.

The tip of dispensing catheter 20 is preferably provided with a radiopaque marker 42, (see FIG. 3) to aid in positively locating and positioning the distal end of catheter 20 in the root of the aorta.

A liquid-tight sliding seal is provided between dispensing catheter 20 and IAB lumen 18 and is comprised of a cylindrical-shaped member 44, preferably formed of a resilient material such as Teflon, having a low coefficient of sliding friction. Cylinder 44 is provided with a pair of outwardly directed flanges 44a and 44b for anchoring member 44 within cooperating recesses 18b, 18c provided in lumen 18 which recesses preferably have a shape conforming to the flanges 44a and 44b. Dispensing catheter 20 is slidable along lumen 18. However, the sliding seal between the external periphery of dispensing catheter 20 and the internal surface of sealing member 44 prevents liquid, such as blood from passing through the seal. Lips 44d and 44e cooperate with lumen 18 to form a liquid-tight sliding seal against the pressure of fluid in the region of the seals.

In order to prevent the dispensing catheter 20 from being telescoped into IAB 10, either accidentally or deliberately, a blocking member 46 is arranged a spaced distance inward from the distal end of dispensing catheter 20. Member 46 may have a cylindrical shape and an outer diameter sufficient to prevent dispensing catheter 20 from being completely telescoped into lumen 18.

In another preferred embodiment shown in FIGS. 4a and 4b, the blocking member 46' has a cone-shaped configuration whose larger diameter end is substantially compressed when being moved through lumen 18 toward and out of tip 14 of IAB 10. Once the blocking member 46' is free of the open end of tip 14, the larger diameter end of cone-shaped blocking member 46' expands so that its left-hand end 46a' has an outer diameter greater than the diameter of the central opening in lumen 18, preventing dispensing catheter 20 from being fully telescoped into lumen 18.

The treatment scheduling of intra-aortic balloon support in combination with dispensing of a blood thinner allows a safer time frame for subsequent study and intervention, whether the intervention be by surgical vein-grafting or balloon catheter dilatation.

Although introduction of a blood thinner does induce bleeding, the use of a percutaneous balloon system with the introducer/dilator retained so as to achieve a good wedging position into the artery, serves as a "hemostatic seal" to combat such bleeding.

Adjustable delay means 32 provides a means for assuring that dispensing of the blood thinner occurs within the desired portion of each diastolic inflationary phase.

Although the preferred embodiment shows the dispensing catheter extending through the central lumen 18, the dispensing catheter may be independently inserted into the aortic arch, side by side with IAB 10.

The dispensing catheter 20 may also be a dual-lumen catheter to serve the dual purpose of coronary dilatation, as well as dispensing medicinal solutions, as shown in FIG. 5.

Here, the dispensing catheter 20 extends beyond the open distal end of lumen 18 and has one lumen 53a for dispensing medicinal solutions through opening 53b. A second lumen 56a serves to inflate the small coronary dilatation balloon 56. As an alternative, the opening for dispensing medicinal solutions could be not only at the distal end 59 of the catheter 20, but at its proximal end, as shown by 56c.

A latitude of modification, change and substitution is intended in the foregoing disclosure, and in some instances some features of the invention will be employed without a corresponding use of other features. Accordingly, it is appropriate that the appended claims be construed broadly and in a manner consistent with the spirit and scope of the invention herein.

What is claimed is:

1. An intraaortic balloon pumping and dispensing catheter system for treating multiple cardiac conditions comprising:
    a balloon assembly comprising an elongated non-stretchable inflatable balloon having a distal end terminating in a tip and having an open proximal end;
    a hollow elongated catheter tube having a distal end communicating with, and gas-tightly sealed, to the proximal end of balloon and having a proximal end for receiving positive and negative pressure pulses for inflating and deflating said balloon;
    an elongated lumen having an open distal end extending into said tip, said lumen extending through said balloon and said catheter tube and having a proximal end extending at least to the proximal end of said catheter tube to facilitate access thereto;
    an elongated hollow dispensing catheter having an outer diameter smaller than the inner diameter of said lumen and movable to position the distal end thereof beyond the open distal end of said lumen to facilitate accurate positioning of the distal end of said dispensing catheter;
    the proximal and distal ends of said dispensing catheter being open to respectively receive a fluid and dispense said fluid to a region adjacent to the distal end of said dispensing catheter and adjustably spaced from the distal end of the balloon;
    cylindrical-shaped seal means in said lumen of smaller diameter than said lumen surrounding and slidably receiving said dispensing catheter for providing a fluid-tight sliding seal between the outer surfaces of said dispensing catheter and the inner surface of said lumen.

2. The system of claim 1 wherein said dispensing catheter is provided with an outwardly extending integral projection a spaced distance inward from the distal end thereof to prevent the dispensing catheter from being fully telescoped into said lumen.

3. The catheter system of claim 1 wherein said dispensing means further comprises a source of said fluid; and
    pump means coupled between said source and the dispensing catheter for pumping a measured amount of fluid from said source into said dispensing catheter.

4. The catheter system of claim 1 wherein said dispensing means further comprises first and second fluid sources;
    pumping means;
    means for coupling the fluids from said first and second fluid sources to said pumping means for pumping the fluids delivered to the pumping means into said dispensing catheter;
    means for adjustably controlling the rate of flow of at least one of said fluids into said pumping means.

5. The catheter system of claim 3 wherein said pumping means comprises a pump having a container through which said fluids pass;
    a flexible diaphram movable by said pump for pumping a fluid into the dispensing catheter.

6. The system of claim 1 further comprising first pump means for introducing positive and negative pressure pulses into the catheter tube of said balloon assembly for respectively inflating and deflating said balloon;
    second liquid pump means responsive to said first pump means for pumping liquid into said dispensing catheter.

7. The system of claim 6 further comprising adjustable delay means for controlling the activation of said second pump and adjustable delay interval after operation of said first pump means.

8. The system of claim 1 further comprising a guide member disposed in the distal end of said dispensing catheter for aiding in the proper placement of the dispensing catheter within the body.

9. The system of claim 8 wherein said guide member comprises a radiopaque marker.

10. Medical apparatus for treating multiple conditions comprising:
    a balloon assembly comprising an elongated non-stretchable inflatable balloon having a distal end terminating in a tip and having an open proximal end;
    a hollow elongated catheter tube having a distal end communicating with, and gas-tightly sealed, to the proximal end of balloon and having a proximal end for receiving positive and negative pressure pulses for inflating and deflating said balloon;
    an elongated lumen having an open distal end extending into said tip, said lumen extending through said balloon and said catheter tube and having a proximal end extending at least to the proximal end of said catheter tube to facilitate access thereto;
    an elongated hollow dispensing catheter having an outer diameter smaller than the inner diameter of said lumen and movable to position the distal end thereof beyond the open distal end of said lumen to facilitate accurate positioning of the distal end of said dispensing catheter;
    the proximal and distal ends of said dispensing catheter being open to respectively receive a fluid and dispense said fluid to a region adjacent to the distal end of said dispensing catheter and adjustably spaced from the distal end of the balloon;

means in said lumen surrounding and slidably receiving said dispensing catheter for providing a fluid-tight sliding seal between the outer surfaces of said dispensing catheter and the inner surface of said lumen;

said dispensing catheter being provided with an outwardly extending integral projection a spaced distance inward from the distal end thereto to prevent the dispensing catheter from being fully telescoped into said lumen;

said projection being resilient and being contracted when arranged within the lumen and expanding when released from the lumen to prevent the dispensing catheter from being fully telescoped into the lumen.

11. A method for treating a patient through the coordinated efforts of a dispensing catheter and an intra-aortic balloon having a hollow lumen extending through the catheter and balloon portions of the intra-aortic balloon comprising the steps of:

introducing the intra-aortic balloon into the body and positioning the balloon portion within the aortic arch;

introducing the dispensing catheter into the body through said lumen and slidably positioning the distal end of the dispensing catheter at any desired location displaced from the distal end of the balloon portion;

providing a fluid tight seal in said lumen to prevent fluid from passing through the region between the inner surface of said lumen and the outer surface of said dispensing catheter, especially during relative movement between said lumen and said dispensing catheter;

periodically inflating and deflating the balloon in synchronism with the systolic and diastolic phases of the heart;

periodically introducing a medicinal solution into the dispensing catheter for dispensing same from the distal end of the dispensing catheter to a particular region of the body displaced from the distal end of the balloon portion.

12. The method of claim 11 wherein the medicinal solution dispensed in a blood thinner and the region in which it is dispensed is one of the coronary arteries.

13. The method of claim 11 further comprising the steps of introducing a guide wire into the body; and guiding the intra-aortic balloon into the body by introducing the proximal end of the guide wire into the distal end of the central lumen of the intra-aortic balloon and advancing the intra-aortic balloon along the guide wire.

14. The method of claim 13 wherein the proximal end of the guide wire is introduced into the dispensing catheter;

the dispensing catheter is inserted into the proximal end of the intra-aortic balloon lumen and is advanced along the lumen being guided by the lumen and the guide wire.

15. The method of claim 14 further comprising the step of positioning the distal end of the guide wire beyond the distal end of the IAB and to the location to be occupied by the distal end of the dispensing catheter;

advancing the dispensing catheter out of the IAB and along the guide wire to properly position the distal end thereof.

16. An intraaortic balloon pumping and dispensing catheter system for treating multiple cardiac conditions, comprising:

a balloon assembly comprisinhg an elongated non-stretchable inflatable balloon having a distal end terminating in a tip and having an open proximal end;

a hollow elongated catheter tube having a distal end communicating with, and gas-tightly sealed, to the proximal end of balloon and having a proximal end for receiving positive and negative pressure pulses for inflating and deflating said balloon;

an elongated first lumen having an open distal end extending into said tip, said first lumen extending through said balloon and said catheter tube and having a proximal end extending at least to the proximal end of said catheter tube to facilitate access thereto;

an elongated hollow second catheter having an outer diameter smaller than the inner diameter of said first lumen and movable to position the distal end thereof beyond the open distal end of said first lumen to facilitate accurate positioning of the distal end of said second catheter;

cylindrical-shaped seal means in said first lumen of smaller diameter than said lumen for providing a fluid-tight sliding seal between said first lumen and said second catheter;

a dilatation balloon mounted upon the distal end of said second catheter;

the proximal end of said second catheter being open to receive a gas under pressure for inflating said dilatation balloon.

17. The catheter system of claim 16 wherein said second catheter has a second elongated lumen having an open distal end extending to the tip of said dilatation balloon, said second lumen extending through said dilatation balloon and said second catheter;

an elongated hollow dispensing catheter extending through said second lumen and movable to position the distal end beyond the open distal end of said second lumen and having a proximal end receiving a medicinal solution for dispensing the solution at a region adjacent the distal end of said dispensing catheter.

18. The catheter system of claim 16 wherein said second catheter has a second elongated lumen having a distal end extending to the proximal end of said dilatation balloon, said second lumen extending through said second catheter;

said second catheter being movable to position the distal end of said second lumen beyond the open distal end of said first lumen and having a proximal end receiving a medicinal solution for dispensing the solution at a region adjacent the distal end of said second lumen.

* * * * *

UNITED STATES PATENT AND TRADEMARK OFFICE
CERTIFICATE OF CORRECTION

PATENT NO. : 4,569,332

DATED : February 11, 1986

INVENTOR(S) : Peter Schiff and Cary L. Lambert

It is certified that error appears in the above-identified patent and that said Letters Patent are hereby corrected as shown below:

Col. 4, line 39, a --,-- should be inserted after "blood".

Col. 6, line 34, "and" should be --an--.

Col. 8, line 9, "comprising" is misspelled.

Signed and Sealed this

Thirtieth Day of December, 1986

Attest:

DONALD J. QUIGG

Attesting Officer

Commissioner of Patents and Trademarks